(12) United States Patent
Tung et al.

(10) Patent No.: US 6,653,149 B1
(45) Date of Patent: Nov. 25, 2003

(54) SPECIMEN COLLECTION DEVICE AND METHOD

(75) Inventors: Ker-kong Tung, Del Mar, CA (US); Todd Denison Pack, San Diego, CA (US); Yuan Tao, San Diego, CA (US)

(73) Assignee: Applied Biotech Inc., San Diego, CA (US)

( * ) Notice: Subject to any disclaimer, the term of this patent is extended or adjusted under 35 U.S.C. 154(b) by 325 days.

(21) Appl. No.: 09/688,588

(22) Filed: Oct. 16, 2000

(51) Int. Cl.$^7$ ................................................ G01N 1/00
(52) U.S. Cl. ........................ 436/174; 604/317; 604/358; 604/385.01
(58) Field of Search .......................... 436/174; 604/317, 604/358, 385.01

(56) References Cited

U.S. PATENT DOCUMENTS

| | | |
|---|---|---|
| 3,754,287 A | 8/1973 | Taylor |
| 4,101,279 A | 7/1978 | Aslam |
| 4,260,443 A | 4/1981 | Lindsay et al. |
| 4,309,782 A | 1/1982 | Paulin |
| 4,340,706 A | 7/1982 | Obayashi et al. |
| 4,367,750 A | 1/1983 | Levine |
| 4,445,235 A | 5/1984 | Slover et al. |
| 4,507,438 A | 3/1985 | Obayashi et al. |
| 4,541,871 A | 9/1985 | Obayashi et al. |
| 4,554,297 A | 11/1985 | Dabi |
| 4,558,100 A | 12/1985 | Kightlinger et al. |
| 4,590,227 A | 5/1986 | Nakamura et al. |
| 4,673,402 A | 6/1987 | Weisman et al. |
| 4,705,050 A | 11/1987 | Markham |
| 4,732,968 A | 3/1988 | Obayashi et al. |
| 4,769,414 A | 9/1988 | Kightlinger et al. |
| 4,808,379 A | 2/1989 | Wardlaw et al. |
| 4,935,022 A | 6/1990 | Lash et al. |
| 5,147,345 A | 9/1992 | Young et al. |
| 5,260,345 A | 11/1993 | DesMarais et al. |
| 5,268,224 A | 12/1993 | DesMarais et al. |
| 5,318,554 A | 6/1994 | Young et al. |
| 5,337,426 A | 8/1994 | Matusewicz et al. |
| 5,412,819 A | 5/1995 | Matusewicz et al. |
| 5,440,942 A | 8/1995 | Hubbard |
| 5,463,782 A | 11/1995 | Carlson et al. |
| 5,558,840 A | 9/1996 | Jones et al. |
| 5,801,220 A | 9/1998 | Desai et al. .................. 524/13 |
| 5,851,648 A | 12/1998 | Stone et al. |
| 5,886,124 A | 3/1999 | Kightlinger et al. |
| 5,998,695 A | 12/1999 | Roe et al. |
| 6,018,093 A | 1/2000 | Roe et al. |

FOREIGN PATENT DOCUMENTS

| | | | | |
|---|---|---|---|---|
| EP | 1080735 A1 | 3/2001 | ........... | A61L/15/60 |

*Primary Examiner*—Jill Warden
*Assistant Examiner*—Monique T. Cole
(74) *Attorney, Agent, or Firm*—Wood, Herron & Evans, L.L.P.

(57) ABSTRACT

A method and device for collection of a stool specimen. Formation of the device occurs in situ by providing a liquid absorbent polymer to water contained in a toilet bowl. The hydrated polymer forms a matrix that is capable of supported a stool specimen deposited thereon. The method and device provides a simple, economical, and less distasteful means for collecting, sampling and evaluating a stool specimen for diagnosis and/or therapy.

13 Claims, No Drawings

SPECIMEN COLLECTION DEVICE AND METHOD

FIELD OF THE INVENTION

The invention is directed generally to a device and method for the collection of a stool sample.

BACKGROUND OF THE INVENTION

A properly collected sample of stool (feces) is necessary in certain diagnostic assays. For many illnesses, particularly stomach and intestinal tract disorders, examining and testing a patient's feces is needed for diagnostic and treatment purposes. In addition, some postoperative monitoring procedures also require periodic examination of the patient's feces. Pediatricians may instruct parents to monitor various characteristic of their child's feces. For example, fecal material may be macroscopically examined for size, shape, color, odor, consistency, and concretions (gallstones and fecaliths). Gross macroscopic examination can also be directed at finding parasites (whole worms or their fragments), and undigested food, and evaluating the amount of blood, pus, mucus, and fat. Microscopic examination of the fecal material may be for undigested food particles (starch, muscle fibers, elastic fibers, etc.), parasite eggs and segments of parasites, fats, and yeasts. Cultures of fecal material may be taken to determine the presence of bacteria, fungi, viruses and protozoa. Chemical examinations may include the determination of pH and electrolytes, qualitation and quantitation of occult blood, bilirubin and some of its derivatives, ingested iron, trypsin, total fat, fatty acids, vitamin A and carotene, and tests for absorption of lactose and D-xylose.

Collection of the stool by the patient, with or without assistance, is often found to be unpleasant. The stool sample is most favorably obtained from a toilet after defecation. The expelled stool, however, may reside on the bottom of the toilet bowl and, if the stool is semi-liquid, obtaining the sample becomes even more difficult.

Currently, there are two general ways to address the problem of stool collection.

The first method for stool collection is by use of a sheet of flexible material that forms a receptacle, using attachments to secure it to a toilet seat. Some of these devices either have holes, or are made of a mesh-like material which allows liquid to pass through while retaining fecal material. After defecation, the individual obtains a sample from the feces residing on the material, breaks the attachments, and then flushes the remaining feces and material in the toilet. The use of such collection devices requires dexterity and hand contact with both the toilet seat and the device prior to and after defecation.

The second method for stool collection is by use of a sheet material that floats on the water in the toilet bowl. The sheet is hydrophillic and flotation is due either to the action of surface tension or to the generation of contained gas or foam, as disclosed in U.S. Pat. No. 4,705,050. After obtaining a sample from the feces residing on the material, the floating material and remaining fecal material are flushed In the toilet. When adding the sheet material to the toilet, however, the individual's hands are in the bowl, close to the edges and sides of the bowl, thus risking unsanitary contact. Furthermore, the deposit of the stool, or pressure exerted on the stool when obtaining the sample, can cause the sheet and stool to become submerged. This makes the sampling process difficult and contaminates the fecal sample with material present in the toilet bowl.

Another problem with currently available devices is the backup of contaminated water in the toilet bowl. This problem particularly occurs with devices made of hydrophilic sheets with moisture activated foaming material. Such sheets may plug the drainage pipes due to shear mass.

A need thus exists to make the process of obtaining a stool sample simple, easy, and as non-distasteful as possible. A need also exists to minimize or eliminate the potential for unsanitary contact with the toilet bowl itself and its contents (water, chemicals, etc), and to have a collection device that is disposed of in both a simple and environmentally friendly manner.

SUMMARY

The invention is directed to a method for forming a stool collection device, and a method of collecting a stool sample using the inventive device.

A sufficient amount of a liquid absorbent or hydratable polymer is hydrated to form a gel-like matrix in the bowl, simply by adding the polymer to a toilet bowl. This matrix, formed in situ, is capable of supporting stool upon defecation into the prepared bowl. Because the stool is supported on the matrix, it is not contaminated by bowl water and may be easily sampled, collected, or evaluated. The polymer may be, for example, an acrylic acid polymer or a starch graft copolymer of 2-propenenitrile.

The device and method avoids the need for a premanufactured receptacle. Such receptacles have attendant problems, for example, the need for attachment to a toilet seat, which may be difficult for some individuals and which allow for hand contamination during attachment. Such receptacles may also clog pipes if disposed by flushing. In contrast, the inventive device is easily formed without any manipulation by the user, and is readily degraded upon flushing, posing no disposal problems.

The polymer may be added to water contained in any toilet bowl, even bowls containing sanitized water. For additional convenience, the polymer may be pre-measured in packets, which may be dropped into the bowl and which may be easily and discretely carried and used by an individual.

These and other embodiments will be apparent with further reference to the following detailed description and examples.

DETAILED DESCRIPTION

A stool (feces) collection device and method to form and use the collection device is disclosed. The collection device contains a hydratable polymer or resin, also referred to as a liquid absorbent or superabsorbent polymer or resin, that forms a matrix of a gel-like substance when in contact with water, such as water within the toilet bowl itself. The liquid absorbent or superabsorbent polymers and resins are generally acrylamide based and are commercially available. Examples of the polymers and resins that may be used in the invention include the following: polyacrylic acid salts, copolymers of acrylic acid salts and methacrylic acid salts, saponification products of methylacrylate-vinyl acetate copolymers, saponification products of starch-ethylacrylate graft copolymers, starch-acrylic acid graft copolymers, saponification products of starch-methyl methacrylate graft copolymers, acrylate homopolymers, acrylate copolymers, alkali acrylate polymers, crosslinked polyacrylic acid salts, crosslinked copolymers of acrylic acid salts and methacrylic acid salts, crosslinked saponification products of methyl acrylate-vinyl acetate copolymers, crosslinked saponification products of starch-ethyl acrylate graft copolymers, crosslinked starch-acrylic acid salt graft copolymers, crosslinked saponification products of starch methyl methacrylategraft copolymers, crosslinked saponification products of starch acrylonitrile graft copolymers and crosslinked sodium carboxymethyl cellulose, crosslinked products of polyacrylates, crosslinked products of hydrolysates of starch-acrylonitrile graft copolymers, crosslinked products of carboxymethylcellulose, crosslinked products of polyvinyl alcohols, crosslinked products of hydrolysates of methyl (meth)acrylate-vinyl acetate copolymers, crosslinked products of cellulose-sodium acrylate graft copolymers, polyethylene oxide, polyvinyl-pyrrolidine, hydroxyethyl cellulose, hydroxypropylcellulose, polymerized $\alpha,\beta$-unsaturated carboxylic acids, crosslinked acrylic acid salt polymers, saponification products of crosslinked acrylic acid ester-vinyl acetate copolymers, saponification products of crosslinked starch-acrylonitrile graft copolymers, crosslinked polyvinyl alcohols grafted with maleic anhydride, saponified polymers or copolymers or starch graft copolymers of 2-propenenitrile, 2-methyl-2-propenenitrile, saponified crosslinked homopolymers of acrylonitrile or methacrylonitrile, saponified graft copolymers of starch and polyacrylonitrile or polymethacrylonitrile, and combinations thereof. The above materials are disclosed in, for example, U.S. Pat. Nos. 4,340,706; 4,507,438; 4,541,871; 4,558,100; 4,590,277; 4,732,968; 4,769,414; and 5,886,124.

Examples of commercially available absorbent polymers containing acrylic acid polymers that may be used in the invention are Aqua Keep® Polymers, such as Aqua Keep® J-550 (Absorbent Technologies, Inc., Muscatine, Iowa). Examples of starch graft copolymers of 2-propenenitrile that may be used in the invention are the Water Lock® A-100 series and Water Lock® D-223 (Grain Processing Corporation, Muscatine, Iowa). These absorbent polymers are used in the field of sanitation articles such as diapers, menstrual articles, disposable cloths, and in the field of agriculture and horticulture as water retentive materials. However, the primary use of the absorbent polymers in these fields is either to retain a liquid from wetting other articles, such as clothing, or to retain and provide a source of water for botanical life.

The inventive method results in a matrix or device that is conveniently and easily formed in situ, for example, in the toilet bowl, to support and retain a deposited fecal sample. In use, the matrix is formed by adding a sufficient amount of the polymer to the water in the toilet bowl to form the matrix. In one embodiment, between about 10 g to about 30 g of polymer is added to four liters of bowl water. The polymer is preferably added in a granular form to prevent dispersion of the polymer as fines, but may be added in any form, such as a powder as long as it contacts sufficient water for hydration to form the matrix.

Within about one minute after addition of the polymer, the water in the bowl is converted into a gel-like matrix. Conversion to the matrix occurs even in the presence of water that contains chemical disinfectants, sanitizers, etc.

The polymer may be added using any means such as sprinkling, pouring, shaking, depositing, or by any other means as apparent to those skilled in the art. Addition may occur from any convenient distance above the water, which eliminates hand contact with unsanitary portions of the toilet bowl during preparation.

A desired amount of polymer can be removed from a container with some type of measuring device. The prescribed amount can also be pre-measured in a package or container, thus eliminating the measurement step. The prescribed amount can also be packaged in a packet that is simply added to the bowl water. The packet material allows the polymer to contact the bowl water, for example, it may dissolve, disintegrate, etc. upon contact with the water, or the packet may be sufficiently porous to allow water to pass through the material and hydrate the polymer, causing swelling and breaking the packet due to the pressure exerted by the polymer. This would be advantageous, for example, during travel, for use by a child, etc.

One advantage of this invention is that it provides a disposable collection device that enables an individual to accurately and easily remove fecal material deposited on the gel-like matrix in a sanitary manner. Samples of the stool can be easily obtained with a sampling device, such as a stick or spoon, without the stool moving or getting near the edge of the bowl. In addition to conventional stool sampling devices such as the aforementioned stick or spoon, a suction type sampling device such as a pipette with a wide orifice can be used to easily obtain fecal material without dilution of the sample with the bowl water, or contamination from other areas of the toilet bowl.

Another advantage of the inventive method is the formation of a matrix to provide adequate support to prevent submersion of the stool into the toilet bowl water. The gel-like matrix is sturdy enough to withstand pressure during both deposition and sampling of fecal material. The matrix also allows semi-liquid feces to be retained on the surface of the material.

Another advantage is that both the matrix and the stool are easily disposed. Flushing removes both the device and stool without any hand contact, thus making the collecting and sampling process less distasteful. The device can be used in the privacy of the home, in a medical office or institution, or even in a public restroom. This makes travel less troublesome when a stool collection or sample is needed for examination or testing. Still another advantage is that the matrix does not cause plumbing blockage problems since it disintegrates with flushing.

The following examples demonstrate various embodiments of the invention, but should not be construed as limiting the invention in scope.

EXAMPLE 1

About 20 g of Aqua Keepe® J-550, an acrylic acid polymer in a granular form, was added to approximately four liters of water in a toilet bowl. The gel matrix formed in the toilet bowl within one minute. Three potato wedges, approximately 20 g each, representing a solid stool, were dropped onto the matrix from heights ranging from about 10 to about 30 inches. The wedges were easily removed from the gel surface without contaminating the gel surface with the toilet bowl water. The wedges were then dropped back onto the matrix surface without altering the surface, thus demonstrating the robustness of the matrix. Upon flushing, the gel rapidly dissipated and was completely disposed without any backup in the plumbing system.

EXAMPLE 2

About 20 g of Aqua Keeps® J-550 polymer, is added to approximately four liters of water in a toilet bowl. The gel matrix forms within one minute. About 20 g of soft flour dough, with a consistency similar to that of a stool sample and in a cylindrical form, is dropped onto the gel from a height of about 20 inches. Two flat wooden tongue depressors are then used to remove a sample of the dough. The sample is removed without disturbing the gel or contaminating the gel surface with the bowl water.

EXAMPLE 3

The stool collection device was formed using the same procedure as in Example 1. Mustard, representing semi-liquid stools, was squeezed from a bottle onto the gel surface from a height of about 10 inches. A representative sample was easily scooped from the surface.

EXAMPLE 4

About 20 g of Aqua Keep® 10SH-NF, a spherical acrylic acid polymer, is added to approximately four liters of water in a toilet bowl. The gel matrix formed in the toilet bowl within one minute. Three potato wedges, approximately 20 g each, representing a solid stool, are dropped onto the matrix from heights ranging from about 10 to 30 inches. The wedges are easily removed from the gel surface without contaminating the gel surface with the toilet bowl water. The wedges are then dropped back onto the matrix surface without altering the surface, thus demonstrating the robustness of the matrix. Upon flushing, the gel rapidly dissipates and is disposed completely without any backup in the plumbing system.

EXAMPLE 5

About 20 g of Aqua Keep® 10SH-NF polymer is added to approximately four liters of water in a toilet bowl. The gel matrix forms within one minute. About 20 g of soft flour dough with a consistency similar to that of a stool sample and in a cylindrical form is dropped onto the gel from a height of about 10 inches. Two flat wooden tongue depressors are used to remove a sample of the dough. The sample is removed without disturbing the gel or contaminating the gel surface with the bowl water.

EXAMPLE 6

The stool collection device is formed using the same procedure as in Example 4. Mustard, representing semi-liquid stools, is squeezed from a bottle onto the gel surface from a height of about 10 inches. A sample of the representative stool is easily scooped from the surface without disturbing the gel and contaminating the gel surface with bowl water.

EXAMPLE 7

About 20 g of the Water Locke® A-100 polymer, a starch graft copolymer of 2-propenenitrile, is added to about four liters of water in a toilet bowl. The gel matrix forms in the toilet bowl within one minute. Three potato wedges, approximately 20 g each, which represent a solid stool, are dropped onto the matrix from heights ranging from about 10 to about 30 inches. The wedges are easily removed from the gel surface without contaminating the gel surface with the toilet bowl water. The wedges are then dropped back onto the surface without disturbing the gel, thus demonstrating the robustness of the matrix. Upon flushing, the gel rapidly dissipates and is disposed without any backup in the plumbing system.

EXAMPLE 8

About 20 g of Water Lock® A-100 polymer is added to approximately four liters of water in a toilet bowl. The gel matrix forms within one minute. About 20 g of soft flour dough, with a consistency similar to that of stool and in a cylindrical form, is dropped onto the gel from a height of about 10 inches. Two flat wooden tongue depressors are then used to remove a sample of the representative stool. The sample is removed without disturbing the gel or contaminating the gel surface with the bowl water.

EXAMPLE 9

The stool collection device is formed using the same procedure as in Example 7. Mustard, representing semi-liquid stools, is squeezed from a bottle onto the gel surface from a height of about 10 inches. A sample of the representative stool is easily scooped from the surface.

It should be understood that the embodiments of the present invention shown and described in the specification are only preferred embodiments of the inventor who is skilled in the art, and are not limiting in any way. Therefore, various changes, modifications or alterations to these embodiments may be made or resorted to without departing from the spirit of the invention and the scope of the following claims.

What is claimed is:

1. A method for forming a stool collection device comprising providing a polymer to water contained in a toilet bowl, said polymer in an amount sufficient to form in-situ a gel-like matrix capable of supporting stool deposited thereon when hydrated.

2. The method of claim 1 further comprising sampling from said supported stool.

3. The method of claim 1 wherein the polymer is selected from the group consisting of polyacrylic acid salts, copolymers of acrylic acid salts and methacrylic acid salts, saponification products of methylacrylate-vinyl acetate copolymers, saponification products of starch-ethylacrylate graft copolymers, starch-acrylic acid graft copolymers, saponification products of starch-methyl methacrylate graft copolymers, acrylate homopolymers, acrylate copolymers, alkali acrylate polymers, crosslinked polyacrylic acid salts, crosslinked copolymers of acrylic acid salts and methacrylic acid salts, crosslinked saponification products of methyl acrylate-vinyl acetate copolymers, crosslinked saponification products of starch-ethyl acrylate graft copolymers, crosslinked starch-acrylic acid salt graft copolymers, crosslinked saponification products of starch methyl methacrylate graft copolymers, crosslinked saponification products of starch acrylonitrile graft copolymers and crosslinked sodium carboxymethyl cellulose, crosslinked products of polyacrylate, crosslinked products of hydrolysates of starch-acrylonitrile graft copolymers, crosslinked products of carboxymethylcellulose, crosslinked products of polyvinyl alcohols, crosslinked products of hydrolysates of methyl (meth)acrylate-vinyl acetate copolymers, crosslinked products of cellulose-sodium acrylate graft copolymer, polyethylene oxide, polyvinyl-pyrrolidine, hydroxyethyl cellulose, hydroxypropylcellulose, polymerized α,β-unsaturated carboxylic acids, crosslinked acrylic acid salt polymers, saponification products of crosslinked acrylic acid ester-vinyl acetate copolymers, saponification products of crosslinked starch-acrylonitrile graft copolymers, crosslinked polyvinyl alcohols grafted with maleic anhydride, saponified polymers or copolymers or starch graft copolymers of 2-propenenitrile, 2-methyl-2-proenitrile, saponified crosslinked homopolymers of acrylonitrile or methacrylonitrile, and saponified graft copolymers of starch and polyacrylonitrile or polymethacrylonitrile, and combinations thereof.

4. The method of claim 1 wherein the liquid absorbent polymer is selected from the group consisting of an acrylic acid polymer, a starch graft copolymer of 2-propenenitrile, and combinations thereof.

5. The method of claim 1 wherein said sufficient amount of said polymer is contained in a packet.

6. The method of claim 1 wherein said polymer is provided in an amount between about 10 g to about 30 g.

7. The method of claim 1 further comprising evaluating said supported stool.

8. A method for collecting a stool sample comprising providing a hydratable polymer to water contained in a toilet bowl, said polymer in an amount sufficient to form in-situ a gel-like matrix capable of supporting stool deposited thereon when hydrated, and providing said stool sample to said matrix.

9. The method of claim 8 wherein said polymer is provided by adding a packet containing said sufficient amount of said polymer to said toilet bowl.

10. The method of claim 8 wherein said liquid absorbent polymer is selected from the group consisting of polyacrylic acid salts, copolymers of acrylic acid salts and methacrylic acid salts, saponification products of methylacrylate-vinyl acetate copolymers, saponification products of starch-ethylacrylate graft copolymers, starch-acrylic acid graft copolymers, saponification products of starch-methyl methacrylate graft copolymers, acrylate homopolymers, acrylate copolymers, alkali acrylate polymers, crosslinked polyacrylic acid salts, crosslinked copolymers of acrylic acid salts and methacrylic acid salts, crosslinked saponification products of methyl acrylate-vinyl acetate copolymers, crosslinked saponification products of starch-ethyl acrylate graft copolymers, crosslinked starch-acrylic acid salt graft copolymers, crosslinked saponification products of starch methyl methacrylate graft copolymers, crosslinked saponification products of starch acrylonitrile graft copolymers and crosslinked sodium carboxymethyl cellulose, crosslinked products of polyacrylates, crosslinked products of hydrolysates of starch-acrylonitrile graft copolymers, crosslinked products of carboxymethylcellulose, crosslinked products of polyvinyl alcohols, crosslinked products of hydrolysates of methyl (meth)acrylate-vinyl acetate copolymers, crosslinked products of cellulose-sodium acrylate graft copolymers, polyethylene oxide, polyvinyl-pyrrolidine, hydroxyethyl cellulose, hydroxypropylcellulose, polymerized $\alpha,\beta$-unsaturated carboxylic acids, crosslinked acrylic acid salt polymers, saponification products of crosslinked acrylic acid ester-vinyl acetate copolymers, saponification products of crosslinked starch-acrylonitrile graft copolymers, crosslinked polyvinyl alcohols grafted with maleic anhydride, saponified polymers or copolymers or starch graft copolymers of 2-propenenitrile, 2-methyl-2-propenenitrile, saponified crosslinked homopolymers of acrylonitrile or methacrylonitrile, and saponified graft copolymers of starch and polyacrylonitrile or polymethacrylonitrile, and combinations thereof.

11. The method of claim 8 wherein said liquid absorbent polymer is selected from the group consisting of an acrylic acid polymer, a starch graft copolymer of 2-propenenitrile, and combinations thereof.

12. A stool retention device comprising a stool retaining matrix formed in situ by providing a hydratable granular acrylic acid polymer to water contained in a toilet bowl, said matrix capable of retaining stool deposited thereon.

13. A stool retention device comprising a stool retaining matrix formed in situ by providing a hydratable spherical acrylic acid polymer to water contained in a toilet bowl, said matrix capable of retaining stool deposited thereon.

* * * * *

UNITED STATES PATENT AND TRADEMARK OFFICE
CERTIFICATE OF CORRECTION

PATENT NO. : 6,653,149 B1
DATED : November 25, 2003
INVENTOR(S) : Ker-kong Tung, Todd Dension Pack and Yuan Tao It is certified that error appears in the above-identified patent and that said Letters Patent is hereby corrected as shown below:

Column 3,
Lines 4-5, read "...products of starch methyl methacrylategraft copolymers, crosslinked saponification..." and should read -- ...products of starch methyl methacrylate graft copolymers, crosslinked saponification... --.

Column 6,
Lines 62-63, read "...graft copolymers of 2-propenenitrile, 2-methyl-2-proenitrile, saponified..." and should read -- ...graft copolymers of 2-propenenitrile, 2-methyl-2-propenenitrile, saponified... --

Signed and Sealed this

Fifteenth Day of March, 2005

JON W. DUDAS
*Director of the United States Patent and Trademark Office*